US010329209B2

(12) United States Patent
Nieskens et al.

(10) Patent No.: US 10,329,209 B2
(45) Date of Patent: Jun. 25, 2019

(54) PROCESS TO CONVERT SYNTHESIS GAS TO OLEFINS OVER A BIFUNCTIONAL CHROMIUM OXIDE/ZINC OXIDE-SAPO-34 CATALYST

(71) Applicant: Dow Global Technologies LLC, Midland, MI (US)

(72) Inventors: Davy Nieskens, Terneuzen (NL); Aysegul Ciftci Sandikci, Terneuzen (NL); Peter E. Groenendijk, Terneuzen (NL); Andrzej Malek, Midland, MI (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

(21) Appl. No.: 15/769,871

(22) PCT Filed: Sep. 7, 2016

(86) PCT No.: PCT/US2016/050490
§ 371 (c)(1),
(2) Date: Apr. 20, 2018

(87) PCT Pub. No.: WO2017/074558
PCT Pub. Date: May 4, 2017

(65) Prior Publication Data
US 2018/0305272 A1 Oct. 25, 2018

Related U.S. Application Data
(60) Provisional application No. 62/248,585, filed on Oct. 30, 2015.

(51) Int. Cl.
*C07C 1/04* (2006.01)
*C10G 2/00* (2006.01)
*C07C 11/04* (2006.01)
*C07C 11/06* (2006.01)

(52) U.S. Cl.
CPC .............. *C07C 1/043* (2013.01); *C10G 2/334* (2013.01); *C07C 11/04* (2013.01); *C07C 11/06* (2013.01); *C07C 2523/06* (2013.01); *C07C 2523/26* (2013.01); *C07C 2529/85* (2013.01); *C10G 2400/20* (2013.01); *Y02P 30/40* (2015.11)

(58) Field of Classification Search
CPC ........... C07C 1/20; C07C 11/02; C07C 1/043; C07C 11/04; C07C 31/04; C07C 11/06; C07C 2523/06; C07C 2523/26; C07C 2529/85; B01J 23/80; B01J 23/8892; B01J 29/0308; B01J 29/041; B01J 29/85; B01J 35/0006; B01J 37/03; C10G 2400/20; C10G 2/334
See application file for complete search history.

(56) References Cited

U.S. PATENT DOCUMENTS

| | | |
|---|---|---|
| 5,714,662 A | 2/1998 | Vora et al. |
| 8,513,315 B2 | 8/2013 | Kibby |
| 2007/0244000 A1* | 10/2007 | Molinier .......... B01J 23/80 502/300 |
| 2008/0319245 A1 | 12/2008 | Fujimoto et al. |
| 2012/0115966 A1 | 5/2012 | Fu et al. |
| 2015/0232345 A1 | 8/2015 | Fan et al. |

FOREIGN PATENT DOCUMENTS

| | | |
|---|---|---|
| CN | 102320912 A | 1/2012 |
| CN | 103071528 A | 5/2013 |
| CN | 103508828 A | 1/2014 |
| WO | 2010068364 A2 | 6/2010 |
| WO | 2012138415 A1 | 10/2012 |

OTHER PUBLICATIONS

Chen et al., "C2—C4 Hydrocarbons Synthesis from Syngas Over CuO—ZnO—Al2O3/SAPO-34 Bifunctional Catalyst", J. Chem. Technol. Biotechnol., Jan. 19, 2014, DOI 10.1002/jctb.4309.
Dawood et al., "Catalse Bifontionnelle: Hydrocondensation Du Monoxyde De Carbone Sur Cu/Zn-Moredenite", Nouveau Journal de Chimie, 1984, 8, 601-604.
Erena et al., "Study of Physical Mixtures of Cr2O3—ZnO and ZSM-5 Catalysts for the Transformation of Syngas into Liquid Hydrocarbons", Ind. Eng. Chem. Res., 1998, 37, 1211-1219.
Erena et al., "Effect of the Operating Conditions on the Conversion of Synghas to Liquid Hydrocarbons over a Cr2O3—ZnO/ZSM5 Bifunctional Catalyst", J. Chem. Technol. Biotechnol., 1998, 72, 190-196.
Erena et al., "Conversion of Syngas to Liquid Hydrocarbons Over a Two-Component (Cr2O2—ZnO and ZSM-5 Zeolite) Catalyst: Kinetic Modelling and Catalyst Deactivation", Chemical Engineering Science, 2000, 55, 1845-1855.
Erena et al., "Study of the Preparation and Composition of the Metallic Function for the Selective Hydrogenation of CO2 to Gasoline Over Bifunctional Catalysts", J. Chem. Technol. Biotechnol., 2003, 78, 161-166.
International Search Report and Written Opinion pertaining to PCT/US2016/050490 dated Dec. 13, 2016.

(Continued)

*Primary Examiner* — Sharon Pregler
(74) *Attorney, Agent, or Firm* — Dinsmore & Shohl

(57) ABSTRACT

A process for preparing C2 and C3 olefins comprises contacting a feedstream including hydrogen, carbon monoxide, and a bifunctional catalyst in a reaction under certain specified conditions. The catalyst includes as components (1) chromium oxide and zinc oxide mixed metal oxides, and (2) a SAPO-34 molecular sieve. The resulting product of the reaction is relatively high in the target lower olefins and relatively low in less desirable products, including C2 and C3 paraffins, C4+ hydrocarbons, oxygenates, and methane, thereby reducing or eliminating the need for certain previously common and costly separations. The bifunctional catalyst as used in the inventive process also offers improvements in catalyst life in comparison with some methanol-to-olefins catalysts. The process may be carried out as a single unit operation.

9 Claims, No Drawings

(56) References Cited

OTHER PUBLICATIONS

Li et al., "Direct Conversion of Syngas into Hydrocarbons Over a Core-Shell Cr—Zn@SiO2@SAPO-34 Catalys", Chinese Journal of Catalysis, 2015, 36, 1131-1135.

Lok et al., "Silicoaluminophosphate Molecular Sieves: Another New Class of Microporous Crystalline Inorganic Solids", J. Am. Chem. Soc., 1984, 106, 6092-6093.

Liu et al., "Synthesis of SAPO-34 Templated by Diethylamine: Crystallization Process and Si Distribution in the Crystals", Microporous and Mesoporous Materials, 2008, 114, 1-3, 416-423.

Simard et al., "ZnO—Cr2O3+ZSM-5 Catalyst with Very Low Zn/Cr Ratio for the Transformation of Synthesis Gas to Hydrcarbons", Appl. Catal. A: Gen., 1995, 125, 81-98.

Wu et al., "Methanol Conversion on SAPO-34: Reaction Condition for Fixed-Bed Reactor", Appl. Catal. A: Gen., 2004, 260, 63-69.

Ye et al., "Synthesis Optimization of SAPO-34 in the Presence of Mixed Template for MTO Process", Adv. Matl. Research, 2010, 132, 246-256.

Yu et al., "Transformation of Syngas to Light Hydrocarbons Over Bifunctional CuO—ZnO/SAPO-34 Catalysts: The Effect of Preparation Methods", Reaction Kinetics Mechanisms and Catalysis, 2014, 112, 489-497.

* cited by examiner

PROCESS TO CONVERT SYNTHESIS GAS TO OLEFINS OVER A BIFUNCTIONAL CHROMIUM OXIDE/ZINC OXIDE-SAPO-34 CATALYST

CROSS REFERENCE TO RELATED APPLICATIONS

This application claims priority to U.S. Provisional Patent Application Ser. No. 62/248,585 filed Oct. 30, 2015, which is incorporated by reference herein in its entirety.

BACKGROUND

1. Field of the Invention

The present invention relates to the field of producing lower olefins from a carbon-based feedstream. More particularly, the invention relates to producing a product mixture with a significant content of $C_2$ and $C_3$ olefins from a feedstream containing hydrogen and carbon monoxide in the presence of a bifunctional catalyst.

2. Background of the Art

For a number of industrial applications a desirable starting material is a lower olefin, particularly a $C_2$, $C_3$, or combination product that can then be converted to industrially desirable materials, for producing plastics, fuels, and various downstream chemicals. These $C_2$ and $C_3$ materials may be saturated or unsaturated and therefore may include ethylene, propylene, ethane, propane, or combinations thereof. A variety of methods of producing these has been developed, including petroleum cracking of paraffins and various synthetic processes.

For example, some industrial processes converting synthesis gas (syngas) feed to olefins have been developed, among them the well-known Fischer-Tropsch (FT) process wherein a mixture of olefins can be produced along with, primarily, longer chain paraffins. This broad product distribution is unfortunately typical for FT processes, and the selectivity to the desired olefins obtained via the syngas conversion is typically relatively limited. In response to this problem some variations of the FT process have been developed to increase the selectivity to light olefins. For example, WO 2012138415 A1 teaches an FT synthesis wherein a supported, iron-based catalyst is used; the temperature range is narrowed to 300 degrees Celsius (° C.) to 400° C.; pressure is at least 2 megapascals (MPa); and the volumetric ratio of hydrogen to carbon monoxide in the feed is at least 3:1.

In fact, much research has centered around identification of catalysts that can alter selectivity in a variety of olefins-producing processes. Various metals and/or zeolite and metal combinations have been tried, with mixed results. For example, Dawood, et al. (*Nouveau Journal de Chimie*, 8 (1984) 601-604) showed formation of increased amounts of olefins over a Cr/Zn and mordenite hybrid mixture.

Simard, et al., "ZnO-$Cr_2O_3$+ZSM-5 catalyst with very low Cr/Zn ratio for the transformation of synthesis gas to hydrocarbons," *Appl. Catal. A: Gen.*, 125 (1995) 81-98, disclosed the influence of Cr/Zn ratio in hybrid catalysts prepared from ZnO—$Cr_2O_3$ and ZSM-5 for the transformation of syngas to hydrocarbons. Pellets of the compound catalyst were prepared by extrusion with methanol catalyst, zeolite and fused $Al_2O_3$ binder. The catalyst with the lowest zinc content gave the highest yield of liquid hydrocarbons (up to 74 percent (%) of total hydrocarbons). It was also found that the conversion of syngas to methanol was performed primarily on the $Cr_2O_3$ phase, while the $ZnCr_2O_4$ phase had a strong influence in the hydrogenation of intermediate hydrocarbons. A low olefin/paraffin ratio and very low yield to short chain hydrocarbons was achieved.

Erena, et al. published a total of four papers including "Study of physical mixtures of $Cr_2O_3$—ZnO and ZSM-5 catalysts for the transformation of syngas into liquid hydrocarbon," *Ind. Eng. Chem. Res.* 37 (1998) 1211-1219, that studied physical mixtures of $Cr_2O_3$—ZnO and ZSM-5 catalysts for the transformation of syngas into liquid hydrocarbons. The catalyst giving the best compromise between CO conversion and selectivity to gasoline (fraction $C_{5+}$) was determined to be the mixture containing $Cr_2O_3$—ZnO with an atomic Cr/Zn ratio of 2.0. It was observed that higher Zn contents of the catalyst resulted in higher proportions of methane and light paraffins. Increase in Zn content was therefore shown to favor hydrogenation reactions over those of gasoline formation, leading to the transformation of light olefins into paraffins and the termination of the aromatization process. The yield of short chain olefins was relatively low.

Li, et. al, "Direct conversion of syngas into hydrocarbons over a core-shell Cr—Zn@$SiO_2$@-SAPO-34 catalyst," *Chinese J. Catal.* 36 (2015) 1131-1135, disclosed the synthesis of a core-shell structured catalyst constituting Cr—Zn oxide as the core and SAPO-34 as the shell for the conversion of syngas into hydrocarbons with 66.9% $C_2$-$C_4$ hydrocarbons selectivity. Only 8.8% of this mix was made up of $C_2$-$C_4$ olefins.

United States (U.S.) Patent Application Publication 2008/0319245 A1 (Fujimoto, et al.) described a process for producing liquefied petroleum gas (hydrocarbon containing propane or butane as a main component) from carbon monoxide and hydrogen with a catalyst which comprises a methanol synthesis component and a zeolite component. The preferred methanol synthesis catalyst component was one wherein an olefin-hydrogenation component (preferably palladium, Pd) was supported on a Zn—Cr based catalyst, and the zeolite component was preferably a (Pd-supported) β-zeolite catalyst.

U.S. Patent Publication WO 2010/068364 A2 (Kibby, et al.) described a process for converting syngas with a catalyst system comprising GaZSM-5 and ZnO—$Cr_2O_3$ to generate high octane hydrocarbons boiling in the gasoline range.

U.S. Pat. No. 8,513,315 B2 (Kibby, et al.) also targeted high boiling hydrocarbons in the gasoline range, using a ZnO—$Cr_2O_3$ plus ZSM-5 hybrid catalyst combination.

Chinese Patent Publication (CN) 103508828A (Qing-jie Ge, et al.) disclosed preparation of ethane and propane from syngas via a single-step conversion in the presence of a multi-functional catalyst. The multi-functional catalyst was a mixture of a CO hydrogenation catalyst and a molecular sieve catalyst modified with, e.g., palladium, platinum, ruthenium, rhodium, copper, iron, cobalt and/or manganese. The CO hydrogenation catalyst was selected from copper(II) oxide/zinc oxide/aluminum oxide (CuO/ZnO/$Al_2O_3$), copper/zirconium dioxide (Cu/$ZrO_2$), zinc oxide/-chromium (III) oxide (ZnO/—$Cr_2O_3$), palladium/zinc oxide/chromium (III) oxide (Pd/ZnO/$Cr_2O_3$), and/or palladium/cerium(IV) oxide (Pd/$CeO_2$).

Chen, et al., "$C_2$-$C_4$ hydrocarbons synthesis from syngas over CuO—ZnO—$Al_2O_3$/SAPO-34 bifunctional catalyst," *J. Chem. Technol. Biotechnol.*, Jan. 9, 2014 (wileyonlinelibrary.com/jctb) DOI 10.1002/jctb.4309 (8 pages), disclosed production of hydrocarbons from synthesis gas over a bifunctional catalyst containing methanol synthesis catalyst $CuO/ZnO/Al_2O_3$ and SAPO-34 zeolite. Production of $C_2$-$C_4$ hydrocarbons was balanced against coking via temperature alteration. Coking was shown after only 4 hours (h).

Yu, et al., "Transformation of syngas to light hydrocarbons over bifunctional CuO—ZnO/SAPO-34 catalysts: the effect of preparation methods," *Reaction Kinetics Mechanisms and Catalysis*, 112 (Apr. 26, 2014) 489-497, disclosed a bifunctional catalyst including CuO/ZnO and SAPO-34 prepared by two different methods. Different methods were found to have significant effect on catalyst performance, but the product obtained was not high in $C_2$ and $C_3$ paraffins.

Despite the obviously extensive research in this area, problems generally encountered have included unacceptable levels of co-products such as methanol, methane, $C_2$ and $C_3$ paraffins, and/or $C_{4+}$ products, requiring expensive separation and recycle in order to effectively utilize the $C_2$ and $C_3$ olefins for their intended purpose(s). Thus, there remains a need in the art for processes that are effective to produce $C_2$ and $C_3$ olefins, which also result in reduced amounts of methanol, methane, $C_2$+$C_3$ paraffins, and/or $C_4$ and higher products, but which still enable desired levels of feedstream conversion. It is also desirable that a variety of feedstreams may be used resulting in essentially the same or a very similar product distribution, which reduces requirements for feedstream purity and/or feedstream costs. It is also desirable that any catalyst(s) used has/have desirably long lifetimes under processing conditions. Finally, it is desirable that such process minimizes or preferably does not involve production of an intermediate product stream of, for example, methanol, DME or other oxygenates which would then need to be separately converted to the desired hydrocarbon product, i.e., a $C_2$ and/or $C_3$ olefinic product.

SUMMARY OF THE INVENTION

In one embodiment the present invention provides a process for preparing a mixture of lower hydrocarbons, comprising (A) introducing a feedstream into a reactor, the feedstream comprising hydrogen gas and carbon monoxide gas, such that the hydrogen gas is present in an amount of from greater than 33 volume percent to less than 75 volume percent, based on combined volumes of the hydrogen gas and the carbon monoxide gas; and (B) contacting the feedstream and a bifunctional catalyst in the reactor, the bifunctional catalyst having not been reduced prior to the contacting, the bifunctional catalyst comprising as components (1) chromium oxide/zinc oxide mixed metal oxides and (2) a SAPO-34 silicoaluminophosphate molecular sieve; under reaction conditions sufficient to form a product mixture, the reaction conditions comprising (a) a reactor temperature ranging from greater than 300 degrees Celsius to less than 450 degrees Celsius; (b) a pressure ranging from greater than 0.2 megapascal (2.0 bar) to less than 5.0 megapascals (50 bar); the product mixture comprising, as calculated on a hydrogen-free, carbon monoxide-free, and carbon dioxide-free basis; (c) a combined ethylene and propylene content greater than 30 percent by weight; (d) a combined ethane and propane content less than 50 weight percent; (e) a methane content less than 15 weight percent; (f) a combined saturated and unsaturated C4 and higher hydrocarbon content less than 20 weight percent; and (g) an oxygenates content less than 5 weight percent; each weight percentage being based upon total product mixture weight and, when taken together, equaling 100 weight percent.

DETAILED DESCRIPTION OF THE EMBODIMENTS

In general the present invention provides a relatively convenient and efficient means of preparing lower hydrocarbons, and in particular $C_2$-$C_3$ olefins, from a feedstream comprising hydrogen ($H_2$) and carbon monoxide (CO). It uses a bifunctional catalyst and targets the problem of broad product distribution encountered in certain processes, such as FT processes, that convert syngas using iron-containing or cobalt-containing catalysts. These problematic processes in general may produce a comparatively wider product distribution (frequently olefins, paraffins, and oxygenates with carbon numbers ranging from $C_1$ to $C_{20+}$); a comparatively lower yield to short chain olefins; and significant methane production.

The present invention also successfully tackles one particular problem related to the MTO process, which is that catalysts used therein typically have relatively short lifetimes and therefore must be rapidly regenerated. The present invention, by comparison, offers a significantly greater catalyst lifetime, in some cases by a factor of more than 10, than many traditional MTO catalysts. For further discussion of MTO catalyst deactivation, see, e.g., X. Wu, et al., "Methanol conversion on SAPO-34: reaction condition for fixed bed reactor," *Appl. Catal. A: Gen.* 260, 63-69, 2004 and U.S. Pat. No. 7,166,757 B2.

Finally, the present invention is operable in a single unit, which may reduce or eliminate costs and the problems associated with multiple unit operations. One example of such a multiple unit operation for producing olefins is MTO processes, which require a two-step protocol wherein methanol is produced first, and then the methanol is used to make the lower olefins. This may be further complicated by addition of a third step, i.e., a (higher) olefins cracking process (OCP). In contrast, the present invention is capable of producing comparable or higher amounts of the $C_2$ and $C_3$ olefins via a single step.

In order to practice the process of the invention, it is first necessary to select an appropriate feed for conversion. The above process has utility in that it converts a feedstream that comprises, consists essentially of or consists of $H_2$ gas and CO gas, to a product mixture that desirably comprises a combination of, in particular, unsaturated two carbon atom and three carbon atom hydrocarbons, that is, $C_2$ and $C_3$ olefins. The product mixture itself has utility as a starting material or intermediate to produce a range of chemical products including plastics, commodity chemicals, and the like. As will be recognized by those skilled in the art, there is often an additional component that may be present in the feed, including in particular a minor proportion of carbon dioxide ($CO_2$) (which is often, although not always, a component of syngas), and/or inerts such as nitrogen ($N_2$), or additional carbon-containing compounds such as methane ($CH_4$), and/or another hydrocarbon, such as a small amount of ethane ($C_2H_6$) or ethylene ($C_2H_4$). In all cases the outlet stream may contain CO, $CO_2$, water ($H_2O$), and $H_2$ originating from unconverted feedstream components, the Water Gas Shift reaction (which produces $CO_2$ and $H_2$, and/or the reverse of the Water Gas Shift reaction (which produces CO and $H_2O$). [The Water Gas Shift reaction is an equilibrium reaction.] It will be well recognized by those skilled in the art that control of feedstream composition can be used to help tailor the final product toward the more desired products.

More specifically, it will be understood that CO will be present in the feedstream in an amount of at least 50 mole-percent (mol %), preferably at least 60 mol %, more preferably at least 70 mol %, still more preferably at least 80 mol %, and most preferably at least 90 mol %, based on total feedstream, excluding $H_2$ gas. This means that inerts, such as nitrogen or noble gases, and/or methane, and/or other carbon-containing compounds, such as $CO_2$, methane, and other hydrocarbons, may be present, in total, in an amount less than or equal to 50 mol %, preferably not greater than 40 mol %, more preferably not greater than 30 mol %, still more preferably not greater than 20 mol %, and most preferably not greater than 10 mol %, based on total feedstream, excluding $H_2$ gas. The $H_2$ gas is separately measured and is desirably present in the total feedstream in a volumetric ratio of $H_2$ to CO ($H_2$:CO) that is greater than 0.5:1, preferably greater than or equal to 0.6:1, and more preferably greater than or equal to 1:1. Such amount is also less than 3:1, and preferably less than or equal to 2:1.

The present invention also employs a particular bifunctional catalyst that, in combination with certain process parameters and with a selected feedstream, produces a particularly desirable and surprising product mix, wherein the yield of target $C_2$ and $C_3$ products is increased, while the yield of $C_2$ and $C_3$ paraffins, $C_{4+}$ hydrocarbons, oxygenates, and methane products is desirably reduced, in comparison with some other $C_2$-$C_3$ olefin targeted processes. Furthermore, this bifunctional catalyst shows a relatively stable conversion over time in the inventive process.

In order to accomplish such, the bifunctional catalyst includes two components. The first component is the mixed metal oxides component, which is alternatively termed a "syngas-to-methanol, or methanol synthesis, component." This component of the bifunctional catalyst comprises, consists essentially of, or consists of both chromium oxide ($Cr_2O_3$) and zinc oxide (ZnO). Because of the nature of mixtures of oxides, this component is assumed to always or virtually always also include phases wherein an oxygen atom or an oxide moiety may be bound covalently to at least one chromium atom or chromium moiety and, at the same time, at least one zinc atom or zinc moiety. Materials wherein the bonding is undetermined may be termed as generally "mixed phases," and written for purposes of convenience, as well as to include both distinct $Cr_2O_3$ and ZnO phases and the "mixed phases" described hereinabove, as "Cr/Zn oxides." Such phases may form and reform as the bifunctional catalyst is used in the inventive process.

The second, equally important, component of the bifunctional catalyst is a microporous crystalline material having an 8-member ring pore opening structure defined by the Structure Commission of the International Zeolite Association (IZA) as CHA. More particularly, the component is an isostructural member of the CHA grouping that is known as SAPO-34 molecular sieve. Because the ring structure of SAPO-34 is known, it is also known that its pore opening has a diameter of approximately 3.8 Angstroms (Å), i.e., 0.38 nanometer (nm). This SAPO-34 molecular sieve is a silicoaluminophosphate material having a silicon content of at least 0.01 wt %, preferably at least 0.1 wt %, and more preferably at least 0.5 wt %, based on total weight of the SAPO-34. For purposes hereof, SAPO-34 molecular sieves will be defined as having a silicon content of at least 0.5 wt %, based on the total weight of the SAPO-34. Other than the substitution of at least the 0.5 wt % silicon in the crystal lattice that would otherwise be an aluminophosphate lattice, the SAPO-34 used in the present invention preferably does not include any other metal atoms, i.e., heteroatoms, in significant amounts, although trace amounts of other metals, such as may result from the preparation process, would not be sufficient to significantly alter the efficacy and overall effect of inclusion of the SAPO-34 in the present invention. As the term is used herein, "trace amounts" represent amounts less than 1.0 wt %, preferably less than 0.5 wt %, more preferably less than 0.1 wt %, and most preferably less than 0.005 wt %. Accordingly, it will be understood by those skilled in the art that the elemental composition of the anhydrous form of SAPO-34 may be represented as $(Si_xAl_yP_z)O_2$, where x, y and z represent molar fractions of silicon, aluminum and phosphorus, with x+y+z=1. See, for example, Lok, B. M., et al., "Silicoalumino-phosphate Molecular Sieves: Another New Class of Microporous Crystalline Inorganic Solids," *J. Am. Chem. Soc.* 106 (1984) 6092-6093.

Notwithstanding the above, the SAPO-34 may be used preferably in its acid form. Those skilled in the art will easily understand that in its acid form the cations charge balancing the framework consists predominantly of proton ions $H^+$. In other embodiments some fraction of the $H^+$ ions can be substituted with other ions, for example, those of the alkaline or alkali group of metals, or other metals such as, in particular, the chromium or zinc.

In preparing the bifunctional catalyst it is necessary to, in one step, obtain or prepare the mixed metal oxides component. These two oxides ($Cr_2O_3$ and ZnO) may be made separately and then combined, or they may be made at the same time in a single reaction process, such as will be well-known and understood by those skilled in the art. It is generally preferred that, in one embodiment, the chromium content independently ranges from greater than 0 wt % to 68 wt % and the zinc content independently ranges from greater than 0 wt % to 80 wt %. Each of the weight percents is based upon the combined weight percents of all metals in the mixed metal oxides. The oxygen, in the form of an oxide moiety, in each catalyst is therefore present in an amount deter-mined by subtracting the sum of the weight percent of each of the component metals from 100 wt %. In the embodiments shown in the examples, the mixed metal oxides component comprises 27 wt % $Cr_2O_3$ (19 wt % Cr) and 73 wt % ZnO (59 wt % Zn).

Notwithstanding the above, it is preferred that the constituents of the mixed metal oxides component be consistently measured in terms of atomic, i.e., molar, ratios, to avoid small inconsistencies that may arise when both weight percent ratios and mole ratios are employed and/or when rounding is carried out in a conversion. For example, in one embodiment the chromium and zinc contents in the mixed metal oxides component are such that the atomic (molar) ratio of chromium to zinc ranges from 0.05:1 to 30:1. More preferred is a range of from 0.07:1 to 20:1, and most preferred is a range of from 0.1:1 to 10:1.

In another (non-ordered) step, the SAPO-34 component may be prepared, prior to combining it with the mixed metal oxides component, via a templating method that is well-known to those skilled in the art. For further discussion, see, e.g., U.S. Patent Application Publication 2015/0232345; G. Liu, et al., "Synthesis of SAPO-34 templated by diethylamine: Crystallization process and Si distribution in the crystals," *Microporous and Mesoporous Materials*, 114 (2008) 1-3, 416-423; Online publication of International Zeolite Association www.iza-online.org/synthesis/-Recipes/SAPO-34.html (includes XRD pattern); and/or L. P. Ye, et al., "Synthesis Optimization of SAPO-34 in the Presence of Mixed Template for MTO Process," *Adv. Mad. Research*, 132 (2010) 246-256.

Once the two components have been prepared, they may be mixed together using any means and methods generally known to those skilled in the art to maximize distribution of the components within the bifunctional catalyst, thereby theoretically optimizing their joint effect on any given volume of feedstream. Preferably the components are combined in proportion such that, in the reactor bed (whether fixed, moving and/or fluidized), they will be in a weight/weight (wt/wt) ratio of mixed metal oxides component: SAPO-34 component ranging from 0.1:1, more preferably from 0.5:1, to 10:1, and more preferably to 5:1. This wt/wt ratio is referred to, in Table 1, as the "catalyst ratio."

In the process of the present invention, the selected feedstream is passed into the selected reactor via a heated reactor inlet, and in the reactor typically moves over and/or through the catalyst bed which has been appropriately loaded with the invention's bifunctional catalyst. Reaction conditions must be sufficient to convert at least a portion of the carbon-containing gas, i.e., particularly the predominant CO gas, into the invention's product mixture, which will be described hereinbelow. The conditions under which this process may be carried out comprise, consist essentially of or consist of: (1) a reactor temperature ranging from greater than 300° C. to less than 450° C.; and (2) a pressure ranging from greater than 2 bar (0.2 MPa) to less than 50 bar (5.0 MPa). In preferred embodiments it is also desirable, for reasons of acceptable industrial productivity, for the feedstream's gas hourly space velocity (GHSV) to be greater than 500 reciprocal hours ($h^{-1}$).

As used hereinabove, the phrase "reactor temperature" will be understood to represent either an average reactor temperature, where temperature is measured at more than one location within the reactor, or the sole temperature, where temperature is measured at only one location within the reactor. However, those skilled in the art will recognize that the temperature at different locations within the reactor will almost certainly vary somewhat, according to feedstream component flow rates, catalyst flow where moving/fluidized bed reactors are employed, bed packing, reactor size and geometry, variations in reactor inlet temperatures, and so forth, and will be able to easily adjust process parameters and other means to control "reactor temperature," to ensure that the reactor temperature requirements of the present invention are met. In addition to making modifications of the reaction parameters listed hereinabove, those skilled in the art may also design a given system such that additional and/or alternative means of temperature control, such as the use of a multi-tube heat exchanger, may be employed.

In certain particular embodiments, such reaction conditions preferably comprise, consist essentially of or consist of: (1) a reactor temperature ranging from greater than 300° C., more preferably from 350° C., and still more preferably from 380° C., to less than 450° C., more preferably to 430° C., and still more preferably to 420° C.; (2) a pressure ranging from greater than 2 bar (0.2 MPa), more preferably from 10 bar (1.0 MPa), and still more preferably from 20 bar (2.0 MPa), to less than 50 bar (5.0 MPa), more preferably to 40 bar (4.0 MPa), and still more preferably to 30 bar (3.0 MPa); and (3) a GHSV of greater than 500 $h^{-1}$, more preferably from 800 $h^{-1}$, and still more preferably from 1,000 $h^{-1}$, to less than 12,000 $h^{-1}$, more preferably to 10,000 $h^{-1}$, and still more preferably to 8,000 $h^{-1}$.

The product mixture resulting from the inventive process, following contact between the feedstream and the bifunctional catalyst under the specified reaction conditions, may desirably be relatively high in the target unsaturated $C_2$ and/or $C_3$ products, such as ethylene and/or propylene; relatively low in $C_2$ and/or $C_3$ saturated products; relatively low in $CH_4$; and also relatively low in oxygenated products. In particular embodiments it is also relatively low in $C_{4+}$ products.

More particularly, the product mixture, regardless of the precise composition of feedstream within the given definition, may be characterized as having, as calculated on a CO-free, $CO_2$-free, and $H_2$-free basis, a combined ethylene and propylene content that is more than 30 wt %; a combined ethane and propane content that is less than 50 wt %; a methane content of less than 15 wt %; a combined saturated and unsaturated $C_4$ and higher (i.e., $C_{4+}$) hydrocarbon content of less than 20 wt %; and an oxygenate content of less than 5 wt %; each weight percentage being based upon total product mixture weight and, when taken together, equaling 100 wt %.

In a preferred embodiment, and again, as calculated on a CO-free, $CO_2$-free, and $H_2$-free basis, the combined ethylene and propylene content is more than 46 wt %; the combined ethane and propane content is less than 40 wt %; the methane content is less than 8 wt %; the combined saturated and unsaturated $C_4$ and higher hydrocarbon content is less than 5 wt %; and the oxygenate content is less than 1 wt %; each weight percentage being based upon total product mixture weight and, when taken together, equaling 100 wt %.

Those skilled in the art will recognize that, based upon mass balance, there is presumed to also be a proportion of $C_{5+}$ hydrocarbons in the product mixture that are typically not measured and are, therefore, unaccounted for despite their theoretical presence. In the Examples/Comparative Examples described hereinbelow, the selectivities of the reported products are normalized to (a total of) 100 wt %. This means that the presence of any additional hydrocarbon constituents, including any $C_{5+}$ components, is not included in the total 100 wt % calculation.

In addition to the above hydrocarbon values, the outlet stream will, as will be understood by the skilled artisan, contain proportions of the product mixture and the unconverted feedstream gases, as well as, typically, a significant amount of water resulting from the reactions which take place. The amount of each will vary according to a variety of factors well known to those skilled in the art, including carbon conversion, yield, catalyst productivity, time on stream, and so forth. The unconverted feedstream gases may be separated from the product mixture and, if desired, recycled back into the process again as a portion of the feedstream. Alternatively, such may be disposed of in an environmentally approved and responsible manner, as will be well-known to those skilled in the art. As with the $C_{5+}$ components, if present, such water is also not included in the calculation of product mixture constituents.

Examples/Comparative Examples 1-16*

*Comparative Examples as marked.
A $Cr_2O_3$/ZnO catalyst is prepared as follows:
Targeting a Cr to Zn molar ratio of 0.4:1 (27 wt % $Cr_2O_3$ and 73 wt % ZnO), appropriate quantities of $Cr(NO_3)_3 9H_2O$ and $Zn(NO_3)_2.H_2O$ are added to distilled water ($H_2O$). In addition, a 0.5 M solution of $(NH_4)_2CO_3$ is prepared as a precipitating agent. The cation ($Cr^{3+}/Zn^{2+}$) and anion (($CO_3)^{2-}$) solutions are simultaneously added dropwise to a stirred beaker of distilled $H_2O$ maintained at 7.0<=pH<=7.5 and T=338+/−5 K. Co-precipitated materials are filtered, washed with distilled water, dried in static air at 383 K, and subsequently calcined at 873 K for 2 h. For Example 16, catalyst synthesis is slightly modified to achieve a Cr/Zn molar ratio of 2:1 (65 wt % $Cr_2O_3$ and 35 wt % ZnO).

The prepared $Cr_2O_3$/ZnO catalyst is then physically mixed with a silicoaluminophosphate catalyst (SAPO-34) by taking appropriate amounts to reach the weight ratio as indicated in Table 1 hereinbelow and shaking them together in a bottle. Each of the catalysts has a particle size before mixing within a range of from 40 U.S. mesh (0.422 mm) to 80 U.S. mesh (0.178 mm). The system is pressurized with pure $N_2$ up to the value as indicated in Table 1. The system is then heated to the value as indicated in Table 1 while still flowing pure $N_2$. The flow of $N_2$ is switched off and certain amounts of CO, $H_2$ and helium (He) are passed over the catalyst to reach the feed ratio and GHSV as indicated in the table. The results are shown in Table 1.

tive Example 5 demonstrates that, while keeping all other parameters the same as in Example 1, an increase in $H_2$:CO ratio from 2 to 3 results in decreased selectivity to $C_2$ and $C_3$ olefins and an increased selectivity to $C_2$ and $C_3$ paraffins at similar conversion levels.

(Comparative) Example 6 shows that, while keeping all the other parameters the same as in Comparative Example 5, an increase in pressure from 20 bar (2.0 MPa) to 50 bar (5.0 MPa) results in a further decrease in $C_2$ and $C_3$ olefins selectivity with an increase in $C_2$ and $C_3$ paraffins selectivity and CO conversion.

(Comparative) Example 7 shows that, while keeping all other parameters the same as in Comparative Example 6, a decrease in catalyst ratio from 2 to 1 leads to even more decreased $C_2$ and $C_3$ olefins selectivity at similar conversion

TABLE 1

Screening of $Cr_2O_3$/ZnO + SAPO-34 catalyst at varying pressures, temperatures, catalyst ratios, $H_2$:CO ratios and GHSVs.

| Examples | T (° C.) | P (bar/MPa) | Catalyst ratio$^{CR}$ (wt/wt) | GHSV ($h^{-1}$) | $H_2$:CO (v/v) | TOS (hr) | CO CONV (%) | $CH_4$ | $C_2H_4 + C_3H_6$ | $C_2H_6 + C_3H_8$ | $C_{4+}$ | Oxygenates |
|---|---|---|---|---|---|---|---|---|---|---|---|---|
| 1 | 400 | 20/2.0 | 2 | 1019 | 2 | 21 | 43.3 | 7.9 | 51 | 36.3 | 4.8 | 0 |
|  |  |  |  |  |  | 100 | 43.1 | 13.9 | 32.6 | 45.9 | 7.5 | 0 |
| 2 | 400 | 20/2.0 | 5 | 1019 | 2 | 6 | 36.7 | 5.2 | 52.4 | 37.7 | 4.6 | 0 |
|  |  |  |  |  |  | 21 | 33.5 | 7.7 | 48.7 | 38.5 | 5 | 0 |
|  |  |  |  |  |  | 100 | 32.7 | 13.9 | 33.8 | 46 | 6.2 | 0 |
| 3 | 400 | 20/2.0 | 2 | 1019 | 1.5 | 21 | 34.5 | 10.7 | 45.3 | 39 | 5 | 0 |
| 4 | 400 | 20/2.0 | 2 | 8151 | 2 | 6 | 10.1 | 5.7 | 70.1 | 19.9 | 4.4 | 0 |
| 5 $^C$ | 400 | 20/2.0 | 2 | 1019 | 3 | 13 | 50.3 | 9.5 | 20.4 | 61.6 | 8.6 | 0 |
|  |  |  |  |  |  | 21 | 50.0 | 10.1 | 19.6 | 61.3 | 9 | 0 |
|  |  |  |  |  |  | 100 | 47.8 | 14.1 | 7.9 | 64.8 | 13.2 | 0 |
| 6 $^C$ | 400 | 50/5.0 | 2 | 1019 | 3 | 21 | 75.9 | 5.9 | 4.6 | 75.9 | 11.8 | 1.7 |
|  |  |  |  |  |  | 101 | 74.4 | 6.8 | 5.2 | 75.1 | 12.2 | 0.8 |
| 7 $^C$ | 400 | 50/5.0 | 1 | 1019 | 3 | 21 | 72.3 | 11.6 | 0.9 | 74.9 | 11.5 | 1.1 |
|  |  |  |  |  |  | 98 | 70.4 | 11.6 | 0.5 | 73.7 | 13.4 | 0.8 |
| 8 $^C$ | 400 | 50/5.0 | 2 | 8151 | 3 | 100 | 31.9 | 14.3 | 19.9 | 56.3 | 9.4 | 0 |
| 9 $^C$ | 400 | 70/7.0 | 2 | 1019 | 2 | 21 | 38.1 | 15.9 | 1.2 | 50.7 | 2.8 | 29.3 |
|  |  |  |  |  |  | 100 | 37.4 | 17.5 | 3.8 | 47.3 | 2 | 29.6 |
| 10 $^C$ | 400 | 70/7.0 | 2 | 1019 | 3 | 21 | 80.0 | 14.3 | 1.6 | 71.4 | 11.8 | 1 |
|  |  |  |  |  |  | 100 | 78.8 | 14.5 | 1 | 71.2 | 12.6 | 0.7 |
| 11 $^C$ | 400 | 2/0.2 | 2 | 1019 | 2 | 21 | 0.6 | n.r.$^+$ | n.r. | n.r. | n.r. | n.r. |
|  |  |  |  |  |  | 99 | 1.0 | n.r. | n.r. | n.r. | n.r. | n.r. |
| 12 $^C$ | 450 | 20/2.0 | 2 | 1019 | 2 | 21 | 32.0 | 42.7 | 1.6 | 50.8 | 4.6 | 0.3 |
|  |  |  |  |  |  | 100 | 23.5 | 59.5 | 1.9 | 36.6 | 1.3 | 0.6 |
| 13 $^C$ | 300 | 20/2.0 | 2 | 1019 | 2 | 21 | 2.7 | n.r. | n.r. | n.r. | n.r. | n.r. |
|  |  |  |  |  |  | 100 | 1.9 | n.r. | n.r. | n.r. | n.r. | n.r. |
| 14 $^{C*}$ | 400 | 20/2.0 | 2 | 1019 | 2 | 21 | 37.7 | 11.6 | 9.1 | 65 | 14.4 | 0 |
|  |  |  |  |  |  | 100 | 35.5 | 13.6 | 5.1 | 67.2 | 14.3 | 0 |
| 15 $^{C*}$ | 400 | 50/5.0 | 2 | 2038 | 3 | 21 | 65.4 | 14.5 | 1.9 | 68.4 | 15.2 | 0 |
|  |  |  |  |  |  | 101 | 63.6 | 16.5 | 1.1 | 66 | 16.4 | 0 |
| 16 $^R$ | 400 | 20/2.0 | 2 | 1019 | 2 | 21 | 10.1 | 11.4 | 19.7 | 63.7 | 5.1 | 0 |
|  |  |  |  |  |  | 71 | 8.2 | 8.2 | 45.5 | 42.8 | 3.5 | 0 |

$^C$ Comparative Examples
* These data are obtained with in situ pre-reduction of the catalyst by flowing a mixture of 22.5 mL/min $H_2$ and 11.25 mL/min $N_2$ at 400° C. for 2 h at atmospheric pressure.
$^+$Selectivity data obtained at this CO conversion level are not considered to be reliable (n.r.) and therefore are not reported.
$^R$ Cr/Zn molar ratio of the $Cr_2O_3$/ZnO catalyst is 2.0.
$^{CR}$Catalyst ratio = $Cr_2O_3$/ZnO component to SAPO-34 component Example 1 shows a high selectivity to $C_2$ and $C_3$ olefins and a low methane and $C_{4+}$ selectivity which are within the claimed ranges.

Example 2 demonstrates that, while keeping all the other parameters the same, an increase in catalyst ratio from 2 to 5 results in selectivity values within the claimed ranges.

Examples 3 and 4 show that a slight decrease in $H_2$:CO ratio from 2 to 1.5 or an increase in GHSV from 1019 to 8151 $h^{-1}$ at 400° C., 20 bar (2.0 MPa) and a catalyst ratio of 2 leads to a product mix with selectivities within the claimed ranges.

(Comparative) Examples 5 to 15 show the effect of process conditions outside of the claimed ranges. Comparalevels. (Comparative) Example 8 shows that, while keeping all the other parameters the same as in Comparative Example 6, an increase in GHSV from 1019 to 8151 $h^{-1}$ results in decreased CO conversion with $C_2$ and $C_3$ olefins selectivity outside the claimed ranges.

(Comparative) Example 9 shows that, while keeping all other parameters the same as in Example 1, an increase in pressure from 20 bar (2.0 MPa) to 70 bar (7.0 MPa) leads to higher methane selectivity accompanied by a much lower $C_2$ and $C_3$ olefins selectivity and an increased oxygenates selectivity outside of the claimed ranges at similar CO conversion levels.

(Comparative) Example 10 shows that increasing the $H_2$:CO ratio from 2 to 3 at 70 bar (7.0 MPa) results in increased selectivity to $C_2$ and $C_3$ paraffins at 80% CO conversion.

(Comparative) Example 11 shows that, while keeping all the other parameters the same as in Example 1, a decrease in pressure from 20 bar (2.0 MPa) to 2 bar (0.2 MPa) results in poor CO conversion. The selectivity data at this conversion level are not considered to be reliable and are therefore not reported.

(Comparative) Example 12 shows that, while keeping all the other parameters the same as in Example 1, an increase in temperature from 400° C. to 450° C. leads to a greatly increased methane yield with poor selectivity to $C_2$ and $C_3$ olefins.

(Comparative) Example 13 shows that, while keeping all the other parameters the same as in Example 1, a decrease in temperature from 400° C. to 300° C. results in poor CO conversion.

(Comparative) Example 14 shows that, while keeping all reaction parameters the same as in Example 1, pre-reduction of the catalyst by flowing a mixture of 22.5 milliliters per minute (mL/min) $H_2$ and 11.25 mL/min $N_2$ at 400° C. for 2 h at atmospheric pressure leads to poor $C_2$ and $C_3$ olefins selectivity with an increase in $C_2$ and $C_3$ paraffins selectivity and $C_4$+ selectivity.

(Comparative) Example 15 shows that pre-reduction of the catalyst results in increased $C_2$ and $C_3$ paraffins yield with increased $C_4$+ selectivity outside the claimed ranges at 50 bar, $H_2$:CO ratio 3, GHSV of 2038 $h^{-1}$ and catalyst ratio of 2.

In Example 16, the Cr/Zn ratio of the chromium oxide/zinc oxide mixed metal oxides catalyst is 2 instead of the 0.4 ratio used in all of the other Examples and Comparative Examples. Operating at the same process parameters as in Example 1, such a modification in the formulation of the chromium oxide/zinc oxide mixed metal oxides component results in a product selectivity which meets the invention's product limitations at 71 h time-on-stream (TOS).

The invention claimed is:
1. A process for preparing a mixture of lower hydrocarbons, comprising
(A) introducing a feedstream into a reactor,
the feedstream comprising hydrogen gas and carbon monoxide gas, such that the volumetric ratio of hydrogen to carbon monoxide ranges from greater than 0.5:1 to less than 3:1; and
(B) contacting the feedstream and a bifunctional catalyst in the reactor,
the bifunctional catalyst having not been reduced prior to the contacting,
the bifunctional catalyst comprising as components
(1) chromium oxide/zinc oxide mixed metal oxides and
(2) a SAPO-34 silicoaluminophosphate molecular sieve;
under reaction conditions sufficient to form a product mixture,
the reaction conditions comprising
(a) a reactor temperature ranging from greater than 300 degrees Celsius to less than 450 degrees Celsius;
(b) a pressure ranging from greater than 0.2 megapascals to less than 5.0 megapascals;
the product mixture comprising, as calculated on a hydrogen-free, carbon monoxide-free, and carbon dioxide-free basis
(c) a combined ethylene and propylene content greater than 30 percent by weight;
(d) a combined ethane and propane content less than 50 weight percent;
(e) a methane content less than 15 weight percent;
(f) a combined saturated and unsaturated C4 and higher hydrocarbon content less than 20 weight percent; and
(g) an oxygenates content less than 5 weight percent;
each weight percentage being based upon total product mixture weight and,
when taken together, equaling 100 weight percent.

2. The process of claim 1 wherein the molar ratio of chromium to zinc ranges from 0.05:1 to 30:1.

3. The process of claim 1 wherein the weight ratio of mixed metal oxides component to SAPO-34 component ranges from 0.1:1 to 10:1.

4. The process of claim 1 wherein the reactor temperature ranges from 350 degrees Celsius to 430 degrees Celsius.

5. The process of claim 1 wherein the pressure ranges from 2.0 megapascals to 3.0 megapascals.

6. The process of claim 1 further comprising as a reaction condition a gas hourly space velocity of from greater than 500 reciprocal hours to less than 12,000 reciprocal hours.

7. The process of claim 1 wherein the product mixture comprises, as calculated on a carbon monoxide-free, carbon dioxide-free, and hydrogen-free basis,
(c) the combined ethylene and propylene content is more than 46 weight percent;
(d) the combined ethane and propane content is less than 40 weight percent;
(e) the methane content is less than 8 weight percent;
(f) the combined saturated and unsaturated $C_4$ and higher hydrocarbon content is less than 5 weight percent; and
(g) the oxygenates content is less than 1 weight percent;
each weight percentage being based upon total product mixture weight and, when taken together, equaling 100 weight percent.

8. The process of claim 1 wherein the feedstream further comprises at least one additional gas selected from carbon dioxide, methane, a hydrocarbon other than methane, an inert gas, or a combination thereof, in an amount less than or equal to 50 mole-percent, based on total feedstream excluding hydrogen.

9. The process of claim 1 wherein the bifunctional catalyst consists essentially of:
(1) chromium oxide/zinc oxide mixed metal oxides; and
(2) a SAPO-34 silicoaluminophosphate molecular sieve.

* * * * *